(12) United States Patent
Turner

(10) Patent No.: US 11,779,688 B2
(45) Date of Patent: Oct. 10, 2023

(54) BREAST SHIELD

(71) Applicant: Wayne D Turner, Auburn, CA (US)

(72) Inventor: Wayne D Turner, Auburn, CA (US)

( * ) Notice: Subject to any disclaimer, the term of this patent is extended or adjusted under 35 U.S.C. 154(b) by 0 days.

(21) Appl. No.: 17/904,455

(22) PCT Filed: Jan. 21, 2021

(86) PCT No.: PCT/US2021/070055
§ 371 (c)(1),
(2) Date: Aug. 17, 2022

(87) PCT Pub. No.: WO2022/159245
PCT Pub. Date: Jul. 28, 2022

(65) Prior Publication Data
US 2023/0061709 A1    Mar. 2, 2023

(51) Int. Cl.
*A61M 1/06* (2006.01)

(52) U.S. Cl.
CPC .................................. *A61M 1/064* (2014.02)

(58) Field of Classification Search
CPC ...... A61M 1/064; A61M 1/066; A61M 1/067; A61M 1/06; A61M 1/062; A61J 13/00
See application file for complete search history.

(56) References Cited

U.S. PATENT DOCUMENTS

| | | | | |
|---|---|---|---|---|
| 940,454 A * | 11/1909 | Fowler | ................. | A61M 1/064 604/75 |
| 2,542,505 A * | 2/1951 | Gascoigne | ............. | A61M 1/06 119/14.41 |
| 4,799,922 A * | 1/1989 | Beer | .................... | A61M 1/815 604/74 |
| 5,941,847 A * | 8/1999 | Huber | ................... | A61M 1/066 604/74 |
| 6,461,324 B1 * | 10/2002 | Schlensog | ............... | A61M 1/06 604/74 |
| 7,223,255 B2 * | 5/2007 | Myers | ................... | A61M 1/062 604/74 |
| 7,758,540 B2 * | 7/2010 | Yamashita | ............ | A61M 1/066 604/74 |
| 7,824,363 B2 * | 11/2010 | Myers | .................... | A61M 1/06 604/74 |
| 8,702,646 B2 * | 4/2014 | Garbez | ................. | A61M 1/062 604/74 |

(Continued)

FOREIGN PATENT DOCUMENTS

| | | | |
|---|---|---|---|
| CN | 211068302 U | * | 7/2020 |
| CN | 211068302 U | | 7/2020 |
| WO | WO-2021186006 A1 | * | 9/2021 ............ A61M 1/064 |

*Primary Examiner* — Scott J Medway
(74) *Attorney, Agent, or Firm* — Patent PC; Bao Tran

(57) ABSTRACT

The breast shield is an apparatus for a resting position use by a nursing woman to capture expressed milk while using a breast pump comprising a breast receiving cone with a plurality of holes and a hole plug on the side of said cone for draining expressed milk away from the breast and into an attached tube for collection in a container. The apparatus is optionally configured with a one-way flow valve positioned in the cone above the nipple and below the holes to enable back-flow prevention of expressed milk. The apparatus is optionally configured with a one-way flow valve connected to any of the holes on the side to enable back-flow prevention of expressed milk.

12 Claims, 3 Drawing Sheets

(56) References Cited

U.S. PATENT DOCUMENTS

| | | | |
|---|---|---|---|
| 8,945,046 B2* | 2/2015 | Brittner | A61J 13/00 |
| | | | 604/74 |
| 9,199,018 B2* | 12/2015 | Bauer | H04N 7/185 |
| 9,205,185 B2* | 12/2015 | Schlienger | A61M 1/06 |
| 9,603,982 B2* | 3/2017 | Silver | A61M 1/0697 |
| 10,052,418 B2* | 8/2018 | Simmons | A61M 1/062 |
| 10,080,825 B2* | 9/2018 | Bartlett, II | A61M 1/062 |
| 10,086,120 B2* | 10/2018 | Bartlett, II | A61M 1/062 |
| 10,207,032 B2* | 2/2019 | Bauer | A61M 1/06 |
| 10,335,525 B2* | 7/2019 | Felber | A61M 1/066 |
| 10,426,705 B2* | 10/2019 | Sherman | A61M 39/22 |
| 10,722,624 B2 | 7/2020 | Makower et al. | |
| 10,828,406 B2* | 11/2020 | Huang | A61M 1/0697 |
| 11,298,445 B2* | 4/2022 | Analytis | A61M 1/062 |
| 11,413,381 B2* | 8/2022 | Quackenbush | A61M 1/066 |
| 11,541,156 B2* | 1/2023 | Hwang | A61M 1/064 |
| 2008/0255503 A1* | 10/2008 | Quackenbush | A61M 1/06 |
| | | | 604/74 |
| 2009/0062731 A1* | 3/2009 | Keyong | A61M 1/064 |
| | | | 604/74 |
| 2009/0254028 A1 | 10/2009 | Brittner | |
| 2010/0049122 A1* | 2/2010 | Jaeger-Waldau | A61M 1/066 |
| | | | 604/74 |
| 2011/0071466 A1* | 3/2011 | Silver | A61M 1/067 |
| | | | 604/74 |
| 2013/0023821 A1 | 1/2013 | Khalil et al. | |
| 2014/0288466 A1 | 9/2014 | Alvarez et al. | |
| 2015/0065996 A1* | 3/2015 | Bartlett, II | A61M 1/062 |
| | | | 604/74 |
| 2015/0148783 A1* | 5/2015 | Bartlett, II | A61M 1/062 |
| | | | 604/74 |
| 2016/0256618 A1 | 9/2016 | Embleton | |
| 2016/0296682 A1* | 10/2016 | Phillips | A61M 1/067 |
| 2017/0065753 A1* | 3/2017 | Nowroozi | A61M 1/06 |
| 2017/0095600 A1 | 4/2017 | Sherman et al. | |
| 2020/0061266 A1 | 2/2020 | Makower et al. | |
| 2021/0121614 A1* | 4/2021 | Schlienger | A61M 1/067 |

* cited by examiner

BREAST SHIELD

TECHNICAL FIELD OF THE INVENTION

This invention relates generally to a breast shield in the general form of a cone for the purpose of capturing milk expressed by a nursing woman from a breast while using a breast pump device connectively attached to either or both breasts of a nursing woman enabling a resting (for example in any recumbent, leaning, or sitting body position) use of said breast pump device. This invention relates more specifically to a breast shield in the general form of a cone having a plurality of milk drain holes positioned in side of said breast shield to enable a resting use of said breast pump by a nursing woman. This invention relates more specifically to a breast shield in the general form of a cone having a plurality of milk drain holes positioned in side of said breast shield and a one-way flow valve to enable a back-flow restriction of expressed milk while in a resting use position of said breast pump by a nursing woman.

BACKGROUND

There are available today a plurality of breast shields in the general form of a cone for the purpose of capturing milk expressed by a nursing woman from a breast while using a breast pump device. These breast shields are designed for and enable a collection of expressed milk while the nursing woman is in a vertical or nearly vertical position.

Attempts to use the existing devices while in a resting position result in a mess of spilled milk and frustration. Use of a breast pump in a resting position is not practical given the current state of the art in breast shields.

In light of the foregoing, there is a need for a breast shield with a plurality of holes for use by a nursing woman while in a resting position to capture and drain expressed milk down and away from the breast to enable a resting use by a nursing woman.

Further, in light of the foregoing, there is a need for a breast shield with a plurality of holes and a one-way flow valve for use by a nursing woman while in a resting position to capture and drain expressed milk down and away from the breast to enable a resting use by a nursing woman.

BRIEF SUMMARY OF THE INVENTION

According to a first aspect of the invention, there is a breast shield apparatus for a resting position use by a nursing woman to capture an expressed milk while using a breast pump comprising a breast receiving cone having a breast cup at a breast connection end, a narrowed neck flange, a funnel, and a breast pump connection end at an opposite end of said breast receiving cone comprising a first milk drain hole, a second milk drain hole, and a stopper having a shield attachment end and a milk drain hole plug configured to enable a closing of either said first milk drain hole or said second milk drain hole thereby enabling said nursing woman to use said breast pump to capture said expressed milk while said nursing woman is in said resting position.

According to a second aspect of the invention, there is a breast shield apparatus for a resting position use by a nursing woman to capture an expressed milk while using a breast pump comprising a breast receiving cone having a breast cup at a breast connection end, a narrowed neck flange, a funnel, and a breast pump connection end at an opposite end of said breast receiving cone comprising a first milk drain hole, a second milk drain hole, and a stopper having a shield attachment end and a milk drain hole plug configured to enable a closing of either said first milk drain hole or said second milk drain hole thereby enabling said nursing woman to use said breast pump to capture said expressed milk while said nursing woman is in said resting position, wherein said breast receiving cone further comprises a one-way flow valve for preventing a back-flow of said expressed milk connectively attached to and completely closing said breast receiving cone between said narrowed neck funnel and said breast pump connection end enabling the prevention of said back-flow of said expressed milk while said nursing woman is in said resting position.

According to a third aspect of the invention, there is a breast shield apparatus for a resting position use by a nursing woman to capture an expressed milk while using a breast pump comprising a breast receiving cone having a breast cup at a breast connection end, a narrowed neck flange, a funnel, and a breast pump connection end at an opposite end of said breast receiving cone comprising a first milk drain hole, a second milk drain hole, and a stopper having a shield attachment end and a milk drain hole plug configured to enable a closing of either said first milk drain hole or said second milk drain hole thereby enabling said nursing woman to use said breast pump to capture said expressed milk while said nursing woman is in said resting position, wherein said breast receiving cone further comprises a one-way flow valve device for preventing a back-flow of said expressed milk by connective attachment to either said first milk drain hole or said second milk drain hole enabling the prevention of said back-flow of said expressed milk while said nursing woman is in said resting position.

According to a fourth aspect of the invention, there is a breast shield, for a collection of said expressed milk further comprising a milk flow tube having a milk drain hole connection at a first end and an opening at a second end, a cap, and a milk container wherein said milk flow tube passes said expressed milk through said first milk drain hole or said second milk drain hole into said tube wherein said expressed milk passes through said cap and into said milk container enabling said collection of said expressed milk through said first milk drain hole or said second milk drain hole into said milk container.

According to a fifth aspect of the invention, there is a breast shield, for a collection of said expressed milk further comprising a milk flow tube having a milk drain hole connection at a first end and a one-way collection valve connectively attached to a second end, a cap, and a milk container wherein said milk flow tube passes said expressed milk through said first milk drain hole or said second milk drain hole into said tube wherein said expressed milk passes through said cap and through said one-way collection valve into said milk container enabling said collection of said expressed milk through said first milk drain hole or said second milk drain hole into said milk container.

According to a sixth aspect of the invention, there is a breast shield for a collection of said expressed milk further comprising a milk flow tube having a milk drain hole connection at a first end having a one-way collection valve connectively attached thereto, a second end, a cap, and a milk container wherein said milk flow tube passes said expressed milk through said first milk drain hole or said second milk drain hole into said tube wherein said expressed milk passes through said one-way collection valve through said cap and into said milk container enabling said collection of said expressed milk through said first milk drain hole or said second milk drain hole into said milk container.

According to a seventh aspect of the invention, there is a breast shield wherein said one-way flow valve is alternatively connectively attached externally to said breast receiving cone at either or both said first milk drain hole and said second milk drain hole.

An advantage of the invention is that a nursing woman can use a breast pump while in a resting position. A further advantage of the invention is that a nursing woman can use a breast pump while in a resting position and not spill or lose expressed milk, thereby eliminating the loss of milk and the resulting usual mess (spilled milk) associated with an attempt to use a breast pump while in a resting position.

The invention will now be described, by way of example only, with reference to the accompanying drawings in which:

DETAILED DESCRIPTION

The detailed embodiments of the present invention are disclosed herein. The disclosed embodiments are merely exemplary of the invention, which may be embodied in various forms. The details disclosed herein are not to be interpreted as limiting, but merely as the basis for the claims and as a basis for teaching one skilled in the art how to make and use the invention.

References in the specification to "one embodiment," "an embodiment," "an example embodiment," etcetera indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

It is notoriously well known in the art, whether one prefers the electric breast pump or the manual type, breast pumps can be very beneficial for mothers who must go to work or for those with low milk supply. Expressing milk is a term describing the removal of milk from the woman's breast, either manually or mechanically. Breast pumps mimic a baby's suckling action by sucking the breast in rhythmic fashion, the combination of creating and releasing suction. Breast pumps vary based on mechanical variables and manufacturers, but they all work using the same basic principles. The present invention improves on this by enabling a suckling action in a breast shield due to the centered placement of the one-way valve.

Figure 1:
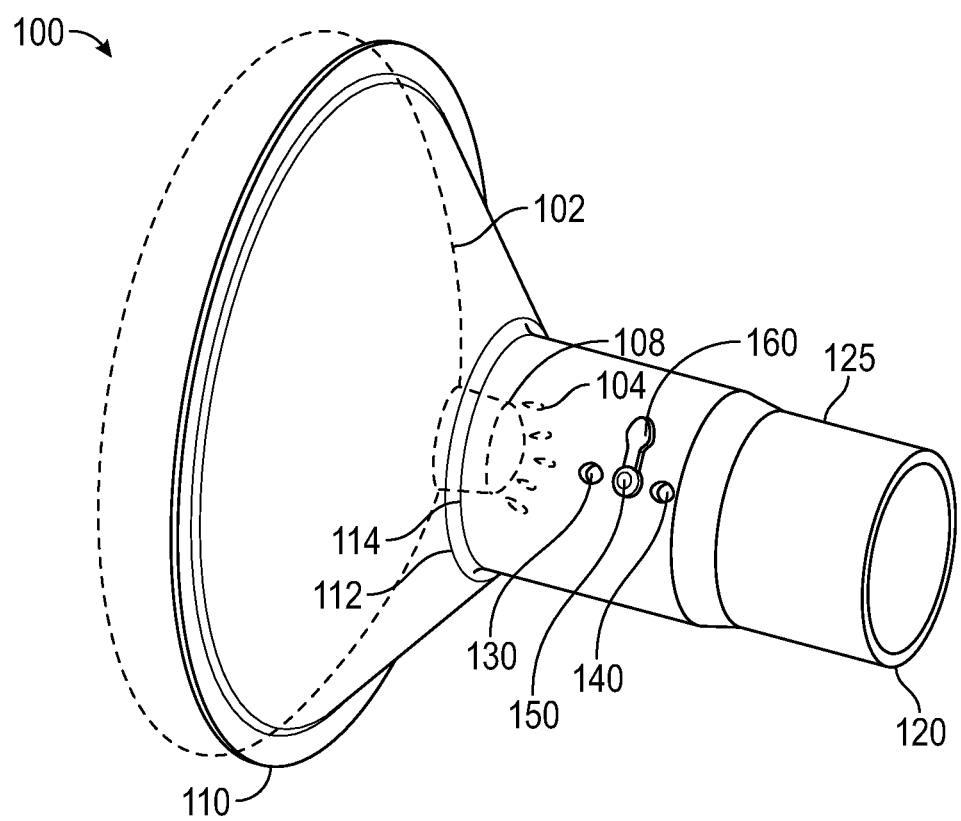
FIG. 1 is a perspective view of the breast shield with milk drain holes according to the invention.
Figure 2:
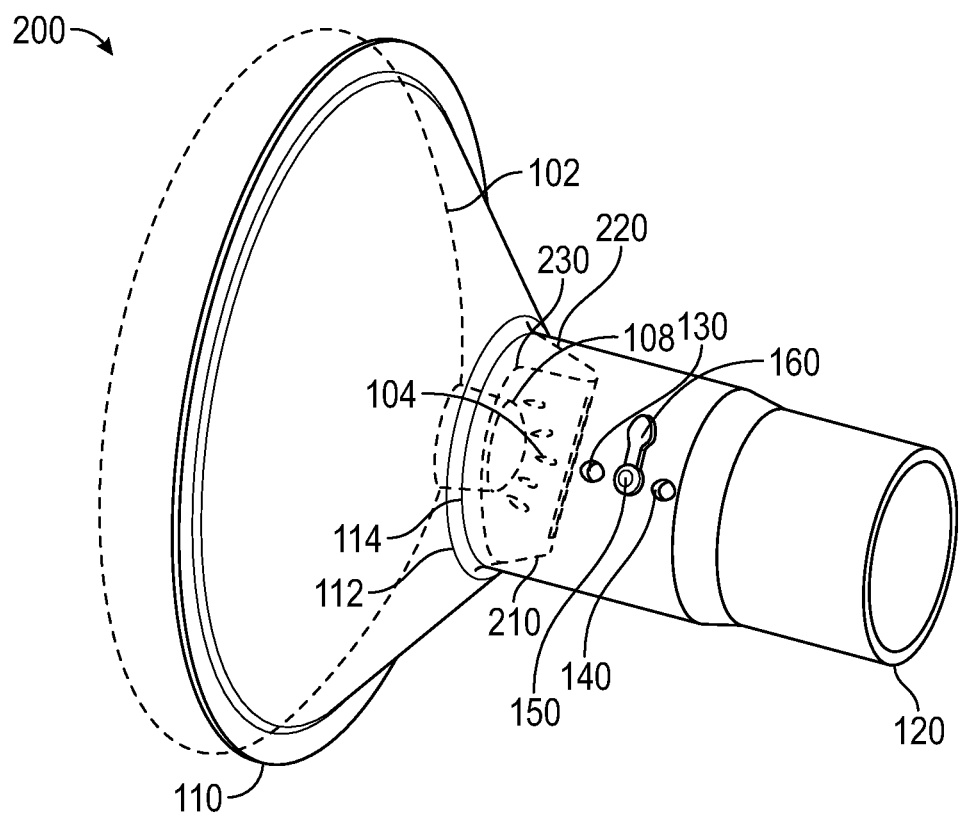
FIG. 2 is a perspective view of the breast shield with a one-way flow valve and milk drain holes according to the invention.
Figure 3:
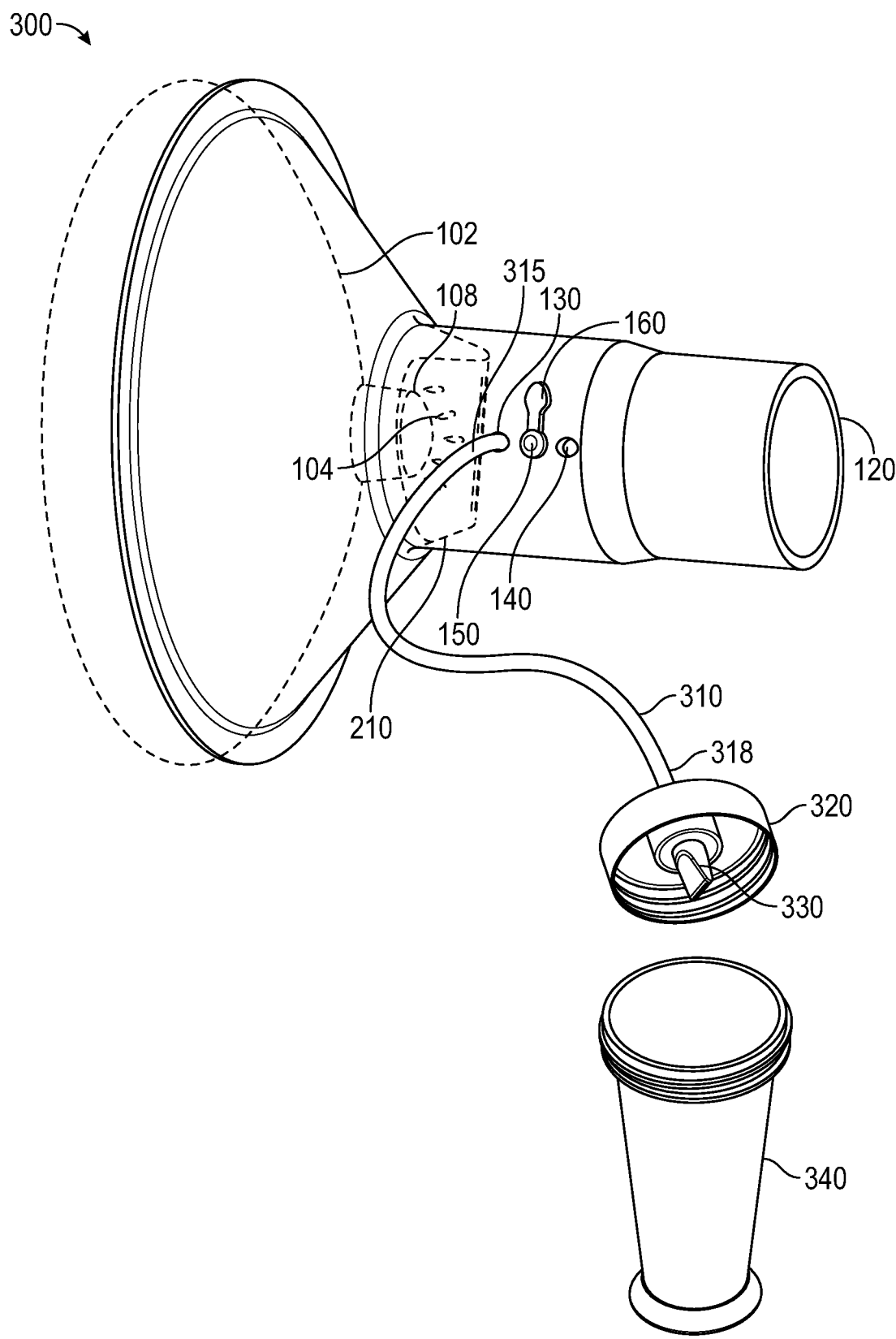
FIG. 3 is a perspective view of the breast shield with a one-way flow valve and milk drain holes according to the invention connected to a tube, cap, and container for collection of expressed milk according to the invention.

Referring to the Figures, there is shown in FIG. 1, Element 100, which is a breast receiving cone (breast shield) according to the present invention. There is shown in FIG. 2, Element 200, which is a breast receiving shield having a one-way back flow preventing valve connectively attached. There is shown in FIG. 3, Element 300 which is a breast receiving shield with an internal one-way back flow preventing valve and the associated drain and capture components to make a milk collection kit.

Index of Labelled Features in Figures (in numeric order)

Element 100 is breast receiving cone version of the breast shield.

Element 102 is a breast.

Element 104 is expressed milk.

Element 108 is a nipple.

Element 110 is a breast connection end of the breast receiving cone (100).

Element 112 is a narrowed neck flange first transition of the breast receiving cone (100).

Element 114 is a narrowed neck flange second transition of the breast receiving cone (100).

Element 120 is a breast pump connection end of the breast receiving cone (100) for connective attachment to a breast pump.

Element 125 is a funnel, or funnel body of the breast receiving cone (100).

Element 130 is a first milk drain hole of the breast receiving cone (100).

Element 140 is a second milk drain hole of the breast receiving cone (100).

Element 150 is the shield attachment end of the stopper.

Element 160 is a milk drain hole plug of the stopper.

Element 200 is a breast receiving cone with one-way flow valve (210) spanning completely across and covering/closing the empty center of the funnel (125) of the breast shield (100) so as to enable preventing a liquid flow back through the one-way flow valve (210).

Element 210 is a one-way flow valve positioned to ensure expressed milk (104) does not return to contact with the breast (102).

Element 220 is a first flap of the one-way flow valve (210).

Element 230 is a second flap of the one-way flow valve (210).

Element 300 is a breast receiving cone, like Element 200, with one-way flow valve spanning completely across and covering/closing the empty center of the funnel (125) of the breast shield (100) with said one-way flow valve so as to prevent back flow of a liquid which is part of a collection kit/package to collect expressed milk while using a breast pump that includes the tubing, cap, and container needed to capture expressed milk (104).

Element 310 is a tube to connect either milk drain hole (130, 140) to a container to enable capture of expressed milk (104).

Element 315 is a milk drain hole connection of the tube (310).

Element 318 is an open end of the tube (310).

Element 320 is a cap.

Element 330 is a one-way container flow valve.

Element 340 is a container to collect expressed milk.

The term recumbent in the context of the present invention is intended to include, at least a person resting in a supine position or a person resting in a position laying, fully or partially on their back or side (left or right) with the front of their body in an upward or partially upward facing direction.

The use of the term "resting" or "resting position" includes, but is not limited to the following: the body of a person being in any recumbent, prone leaned (not completely vertical) back, prone leaned to the left body side, prone leaned to the right body side, or sitting vertical, sitting leaned back, sitting leaned to the left body side, or sitting leaned to the right side body position such that connective attachment of a breast shield to either or both a left breast and a right breast is possible for the purpose of expressing breast milk with the assistance/use of a breast pump to pump breast milk.

Herein the terms "breast receiving cone" and "breast shield" are intended to be synonymous and interchangeable without changing the meaning or context of the language presented. Further, is it noted that use of the term/phrase "nursing woman" includes, but is not limited to the following: any person whose breasts are in a condition to lactate, a nursing mother (mom) breastfeeding a baby, and a nursing surrogate (maid) breastfeeding a baby.

The breast shield (100, 200) features an adjustable range of milk drain holes (130, 140) for milk exiting to accommodate differences in the length of the nipple. The milk drain holes (130, 140) could alternatively be placed in different locations, and/or increased in number to facilitate a plurality of different models with finer and finer degrees of precision as to suitability for specific nipple lengths. The milk drain holes (130, 140) may alternatively be reduced to a single hole without an accompanying stopper (150, 160).

The breast shield (100, 200) features a one-way flow valve (210) having a plurality of flaps, shown as a first flap (220) and second flap (230), wherein the one-way flow valve (210) is positioned covering the interior of the funnel (125) so as to enable expressed milk (104) back flow prevention thereby reducing loss of expressed milk (104) and keeping the breast (102) free of accumulated expressed milk (104). The one-way flow valve (210) thus helps ensure a comfortable and complete expression without the breast (102) becoming wet/saturated with expressed milk (104).

In use, the breast pump connection end (120) is connected to a breast pump and the breast pump is turned on to enable pumping/suction to cause milk to be expressed.

In all embodiments, the breast receiving cone (100, 200) is made from a material that is food grade, sterilizable, washable, and reusable. The one-way flow valve (210) is made from a material that is soft feeling to the sense of touch, food grade, sterilizable, washable, reusable and moves easily and readily to enable opening the one-way flow valve flaps (220, 230) when the one-way flow valve (210) is placed into the inside of the funnel (125) of the breast receiving cone (100) thereby creating the breast receiving cone with one-way flow valve (210) positioned to enable a back flow prevention. The one-way flow valve (210) is positioned above narrowed neck flange (112, 114) and below the milk drain holes (130, 140).

In alternate embodiments, the one-way flow valve (210) is an external device/apparatus that is positioned in, and or connectively attached to a tube (310) and one or both of the milk drain holes (130, 140) to enable a back flow prevention of expressed milk (104) once drawn past said once-way flow valve (210).

In an embodiment, the breast shield (100, 200) is combined with a tube (310) to connect either milk drain hole (130, 140) to a container (340) to enable capture of expressed milk (104) while using the breast receiving cone (100, 200) with a breast pump attached to the breast pump connection end (120). Expressed milk (104) flows out of the breast shield (100, 200) and through the connectively attached milk drain hole connection (315) of the tube (310), through the tube (310) and out the open end (318) of the tube (310). When the tube (310) is inserted through the cap (320) the expressed milk (104) can be collected directly into a container (340) which the cap (320) is connectively attached to.

In an embodiment, a nursing woman (mom) will utilize two breast shields (100 and/or 200) to enable pumping from both breasts for milk to be expressed (pumped) at the same time. The present invention allows for one or two breasts to pump on the side lying, reclining and supine positions. The present invention makes it easier and more comfortable to hold the breast shield (100, 200) in the correct (shield centered around the nipple) position since the woman's arm is resting on the arm of the chair or on the bed if she is not using a hands free pumping bra. It is noted that use of/with a hands free pumping bra to assist in holding the breast shield in the correct nipple centered in the opening position will prevent nipple tissue damage and reduce neck, shoulder and back fatigue and strain by avoiding the need to lean forward when pumping in upright position.

An advantage of using the present invention is that it allows a nursing woman to pump (i.e. use a breast pump to express milk) in a reclined position even if she is unable to tolerate sitting up to pump due to physical and/or medical condition, i.e. headache, hemorrhoids, dizziness, (any condition which would not allow her to tolerate sitting up to pump).

In one embodiment of the invention, there is a breast shield (100) apparatus for a resting position use by a nursing woman to capture an expressed milk (104) while using a breast pump comprising a breast receiving cone (100) having a "breast cup" at a breast connection end (110), a narrowed neck flange (112, 114), a funnel (125), and a breast pump connection end (120) at an opposite end of said breast receiving cone (100) comprising a first milk drain hole (130), a second milk drain hole (140), and a stopper having a shield attachment end (150) and a milk drain hole plug (160) configured to enable a closing of either said first milk drain hole (130) or said second milk drain hole (140) thereby enabling said nursing woman to use said breast pump to capture said expressed milk (104) while said nursing woman is in said resting position.

In an embodiment of the invention, there is a breast shield (200) apparatus for a resting position use by a nursing woman to capture an expressed milk (104) while using a breast pump comprising a breast receiving cone (100) having a breast cup at a breast connection end (110), a narrowed neck flange (112, 114), a funnel (125), and a breast pump connection end (120) at an opposite end of said breast receiving cone (100, 200) comprising a first milk drain hole (130), a second milk drain hole (140), and a stopper having a shield attachment end (150) and a milk drain hole plug (160) configured to enable a closing of either said first milk drain hole (130) or said second milk drain hole (140) thereby enabling said nursing woman to use said breast pump to capture said expressed milk (104) while said nursing woman is in said resting position, wherein said breast receiving cone (100, 200) is further comprises a one-way flow valve (210) for preventing a back-flow of said expressed milk (104) connectively attached to and completely closing said breast receiving cone (100, 200) between said narrowed neck funnel (112, 114) and said breast pump connection end (120)

enabling the prevention of said back-flow of said expressed milk (104) while said nursing woman is in said resting position.

In one embodiment of the invention, there is a breast shield (200) apparatus for a resting position use by a nursing woman to capture an expressed milk (104) while using a breast pump comprising a breast receiving cone (100) having a breast cup at a breast connection end (110), a narrowed neck flange (112, 114), a funnel (125), and a breast pump connection end (120) at an opposite end of said breast receiving cone (100, 200) comprising a first milk drain hole (130), a second milk drain hole (140), and a stopper having a shield attachment end (150) and a milk drain hole plug (160) configured to enable a closing of either said first milk drain hole (130) or said second milk drain hole (140) thereby enabling said nursing woman to use said breast pump to capture said expressed milk (104) while said nursing woman is in said resting position, wherein said breast receiving cone (100) further comprises a one-way flow valve device (210, 220, and 230) for preventing a back-flow of said expressed milk (104) by connective attachment to either said first milk drain hole (130) or said second milk drain hole (140) enabling the prevention of said back-flow of said expressed milk (104) while said nursing woman is in said resting position.

In an alternate embodiment of the invention, there is a breast shield (100, 200) wherein said one-way flow valve (210) is alternatively connectively attached externally to said breast receiving cone at either or both said first milk drain hole (130) and said second milk drain hole (140).

In an alternate embodiment of the invention, there is a breast shield (100, 200) as in any of the previous embodiments further comprising a breast shield (100, 200), for a collection of said expressed milk (104) further comprising a milk flow tube (310) having a milk drain hole connection (315) at a first end and an opening (318) at a second end, a cap (320), and a milk container (340) wherein said milk flow tube (310) passes said expressed milk (104) through said first milk drain hole (130) or said second milk drain hole (140) into said tube (310) wherein said expressed milk (104) passes through said cap (320) and into said milk container (340) enabling said collection of said expressed milk (104) through said first milk drain hole (130) or said second milk drain hole (140) into said milk container (340).

In an alternate embodiment of the invention, there is a breast shield (100, 200) as in any of the previous embodiments further comprising a breast shield (100, 200), for a collection of said expressed milk (104) further comprising a milk flow tube (310) having a milk drain hole connection (315) at a first end having a one-way collection valve (330) connectively attached thereto, and an open end (318), a cap (320), and a milk container (340) wherein said milk flow tube (310) passes said expressed milk (104) through said first milk drain hole (130) or said second milk drain hole (140) into said tube (310) wherein said expressed milk (104) passes through said one-way collection valve (330) through said cap (320) and into said milk container (340) enabling said collection of said expressed milk (104) through said first milk drain hole (130) or said second milk drain hole (140) into said milk container (340)

In an alternate embodiment of the invention, there is a breast shield (100, 200) as in any of the previous embodiments further comprising a breast shield (100, 200), for a collection of said expressed milk (104) further comprising a milk flow tube (310) having a milk drain hole connection (315) at a first end and a one-way collection valve (330) connectively attached to a second end (318), a cap (320), and a milk container (340) wherein said milk flow tube (310) passes said expressed milk (104) through said first milk drain hole (130) or said second milk drain hole (140) into said tube (310) wherein said expressed milk (104) passes through said cap (320) and through said one-way collection valve (330) into said milk container (340) enabling said collection of said expressed milk (104) through said first milk drain hole (130) or said second milk drain hole (140) into said milk container (340).

To begin using the preferred embodiment one of the milk drain holes (130, 140) is closed/stopped with the milk drain hole plug (160) of the stopper (not separately numbered) by rotating the stopper into position above the milk drain hole (130, 140) to be closed (not available for use) and inserting the milk drain hole plug (160) into the milk drain hole (130, 140) thereby closing it. The expressed milk (104) will flow through the cone and through the milk drain hole (130, 140). The expressed milk (104) will flow out of the funnel (125) and pass through the flaps (220, 230) of the one-way flow valve (210) and then out through the milk drain hole (130, 140) where the embodiment of the invention has the one-way flow valve (210) included.

Use of the invention is simple. A breast (102) is inserted into the breast connection end (110) of the breast receiving cone (100). The breast (102) is best positioned such that the nipple (108) is directed pointing upward into the center of the narrowed neck flange (112, 114). This enables expressed milk (104) to be safely drawn up past the one-way flow valve (210) through the flaps (220, 230) where the embodiment includes the one-way flow valve (210). The centered position not only enhances comfort but also ensures that the milk drain hole (130, 140) that is left open is positioned to enable flow of the expressed milk (104) out of the device without impedance.

In any embodiment, the breast receiving cone (100, 200) is commonly known to the general breast pump using/aware public as a "breast shield." In any embodiment wherein a container (340) is used to collect expressed milk (104), said container (340) comprises any of the following: a container, a milk bottle, a nursing bottle, a baby bottle, a bag, a milk bag, a nursing bottle bag, a baby bottle bag, a pitcher and/or a cup.

An advantage of the invention is that a nursing woman with one or more injured, sore, raw, bitten, or sensitive nipples can use a breast pump while in a resting or sitting position. A further advantage of the invention is that said nursing woman with nipple injury or soreness can use a breast pump while in a resting position or sitting position and not spill or lose expressed milk, thereby eliminating lost milk and the resulting usual mess (spilled milk) associated with an attempt to use a breast pump while in a recumbent or sitting position.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

Although the invention has been explained in relation to various embodiments, it is to be understood that many other possible modifications and variations can be made without departing from the spirit and scope of the invention.

The invention claimed is:

1. A breast shield apparatus configured to capture an expressed milk of a nursing woman when operatively attached to a breast pump comprising
a breast receiving cone having:
a breast cup at a breast connection end,
a narrowed neck flange coupled to the breast cup,
a funnel having a first end coupled to the narrowed neck flange and a second opposite end to receive a breast pump connection, wherein the funnel includes a first milk drain hole, a second milk drain hole, and a stopper having a shield attachment end and a milk drain hole plug configured to enable a closing of either said first milk drain hole or said second milk drain hole to enable said nursing woman to use said breast pump to capture said expressed milk while said nursing woman is in a substantially reclined resting position,
wherein said breast receiving cone further comprises a wedge-shaped one-way valve spanning across the first end to cover or close a center of the funnel.

2. The breast shield apparatus of claim 1 wherein said funnel further comprises a second milk drain hole, and a stopper having a shield attachment end and a milk drain hole plug configured to enable a closing of either said first milk drain hole or said second milk drain hole.

3. The breast shield apparatus of claim 1 further comprising a milk flow tube having a milk drain hole connection at a first end and an opening at a second end, a cap, and a milk container.

4. The breast shield apparatus of claim 1 further comprising a milk flow tube having a milk drain hole connection at a first end and a one-way collection valve connectively attached to a second end, a cap, and a milk container.

5. The breast shield apparatus of claim 1 further comprising a milk flow tube having a milk drain hole connection at a first end having a one-way collection valve connectively attached thereto, a second end, a cap, and a milk container configured for a collection of said expressed milk.

6. The breast shield apparatus of claim 1, 2, 3, 4, or 5 configured for a collection of said expressed milk.

7. The breast shield apparatus of claim 1 wherein said nursing woman is in a reclined position.

8. The breast shield apparatus of claim 1 wherein said wedge-shaped one-way valve comprises a bi-valve wedge-shaped body.

9. The breast shield apparatus of claim 1 wherein a body of said wedge-shaped one-way valve defines a triangular valve prism-shaped body.

10. The breast shield apparatus of claim 8 or 9 wherein said body of said wedge-shaped one-way valve defines a nipple-shaped body.

11. The breast shield apparatus of claim 8 or 9 wherein said body of said wedge-shaped one-way valve includes a body extending into said funnel that is configured to receive a breast nipple.

12. A breast shield apparatus configured to capture an expressed milk of a nursing woman when operatively attached to a breast pump, comprising:
a breast receiving cone having:
a breast cup at a breast connection end,
a narrowed neck flange coupled to the breast cup,
a funnel having a first end coupled to the narrowed neck flange and a second opposite end to receive a breast pump connection, wherein the funnel includes a first milk drain hole, a second milk drain hole, and a stopper having a shield attachment end and a milk drain hole plug configured to enable a closing of either said first milk drain hole or said second milk drain hole to enable said nursing woman to use said breast pump to capture said expressed milk while said nursing woman is in a substantially reclined resting position,
wherein said breast receiving cone further comprises a wedge-shaped one-way flow valve configured to receive a breast nipple within the wedge-shaped one-way flow valve.

* * * * *